US009368246B2

(12) United States Patent
Runft et al.

(10) Patent No.: US 9,368,246 B2
(45) Date of Patent: Jun. 14, 2016

(54) CONTROL DEVICE

(75) Inventors: Werner Runft, Winnenden (DE); Iulian Maga, Ludwigsburg (DE); Jens Schlipf, Freiberg A. N. (DE); Martin Vogt, Schorndorf (DE)

(73) Assignee: Robert Bosch GmbH, Stuttgart (DE)

( * ) Notice: Subject to any disclaimer, the term of this patent is extended or adjusted under 35 U.S.C. 154(b) by 209 days.

(21) Appl. No.: 14/111,570

(22) PCT Filed: Mar. 1, 2012

(86) PCT No.: PCT/EP2012/053572
§ 371 (c)(1),
(2), (4) Date: Oct. 14, 2013

(87) PCT Pub. No.: WO2012/139812
PCT Pub. Date: Oct. 18, 2012

(65) Prior Publication Data
US 2014/0037064 A1    Feb. 6, 2014

(30) Foreign Application Priority Data
Apr. 13, 2011 (DE) .......................... 10 2011 007 269

(51) Int. Cl.
*G21K 5/10* (2006.01)
*G01G 9/00* (2006.01)
(Continued)

(52) U.S. Cl.
CPC . *G21K 5/10* (2013.01); *A61J 3/074* (2013.01); *G01G 9/005* (2013.01); *G01G 17/00* (2013.01); *G01N 23/043* (2013.01); *G01N 2223/633* (2013.01); *G01N 2223/652* (2013.01)

(58) Field of Classification Search
CPC ......... G21K 5/10; G02N 223/66; A61J 3/074; G01G 17/00; G01G 9/005; G01N 23/043; G01N 2223/633; G01N 2223/652
See application file for complete search history.

(56) References Cited

U.S. PATENT DOCUMENTS 3,709,598 A * 1/1973 Vandenberg ............ A61J 3/074
209/585
3,942,900 A * 3/1976 Garris ................... B07C 5/3404
250/222.1
(Continued)

FOREIGN PATENT DOCUMENTS

JP          H0815493          1/1996
JP          2000028422        1/2000
(Continued)

OTHER PUBLICATIONS

Machine Translation of WO 2011/047945.*
(Continued)

*Primary Examiner* — Yara B Green
(74) *Attorney, Agent, or Firm* — Michael Best & Friedrich LLP

(57) ABSTRACT

The invention relates to a control device (10) comprising a radiation source (17) which is embodied, in particular, as an X-ray source for irradiating a pharmaceutical product (1) embodied, in particular as a capsule, a detector (18) for detecting radiation after irradiating the pharmaceutical product (1), a tube or shaft-shaped supply device (15) which is preferably arranged vertically at least in the region of the beam path (16) of the radiation source (17) for feeding the pharmaceutical product (1) into the beam path (16) of the radiation source (17), and means (25) for positioning and releasing the pharmaceutical product (1) in the region of the radiation beam (16) of the radiation source (17). According to the invention, the tube or shaft-shaped supply device (15) has a cross-section in the region of the beam path (16) which is greater than the cross-section of the pharmaceutical product (1), and that during irradiation, respectively only one pharmaceutical product (1) is arranged in the region of the beam path (16) of the radiation source (17).

12 Claims, 1 Drawing Sheet

(51) Int. Cl.
*G01G 17/00* (2006.01)
*G01N 23/04* (2006.01)
*A61J 3/07* (2006.01)

(56) References Cited

U.S. PATENT DOCUMENTS

| | | | |
|---|---|---|---|
| 4,117,935 | A | 10/1978 | Richardson et al. |
| 5,819,953 | A | 10/1998 | Julius et al. |
| 6,162,998 | A * | 12/2000 | Wurst et al. .................. 177/145 |
| 7,042,231 | B2 * | 5/2006 | Trebbi .................. G01N 33/15 |
| | | | 209/571 |
| 2010/0170831 | A1 | 7/2010 | Ambroise |

FOREIGN PATENT DOCUMENTS

| | | |
|---|---|---|
| JP | 2005531783 | 10/2005 |
| JP | 2008538003 | 10/2008 |
| JP | 2013532823 | 8/2013 |
| WO | 2011047945 | 4/2011 |

OTHER PUBLICATIONS

International Search Report for Application No. PCT/EP2012/053572 dated May 14, 2012 (2 pages).

* cited by examiner

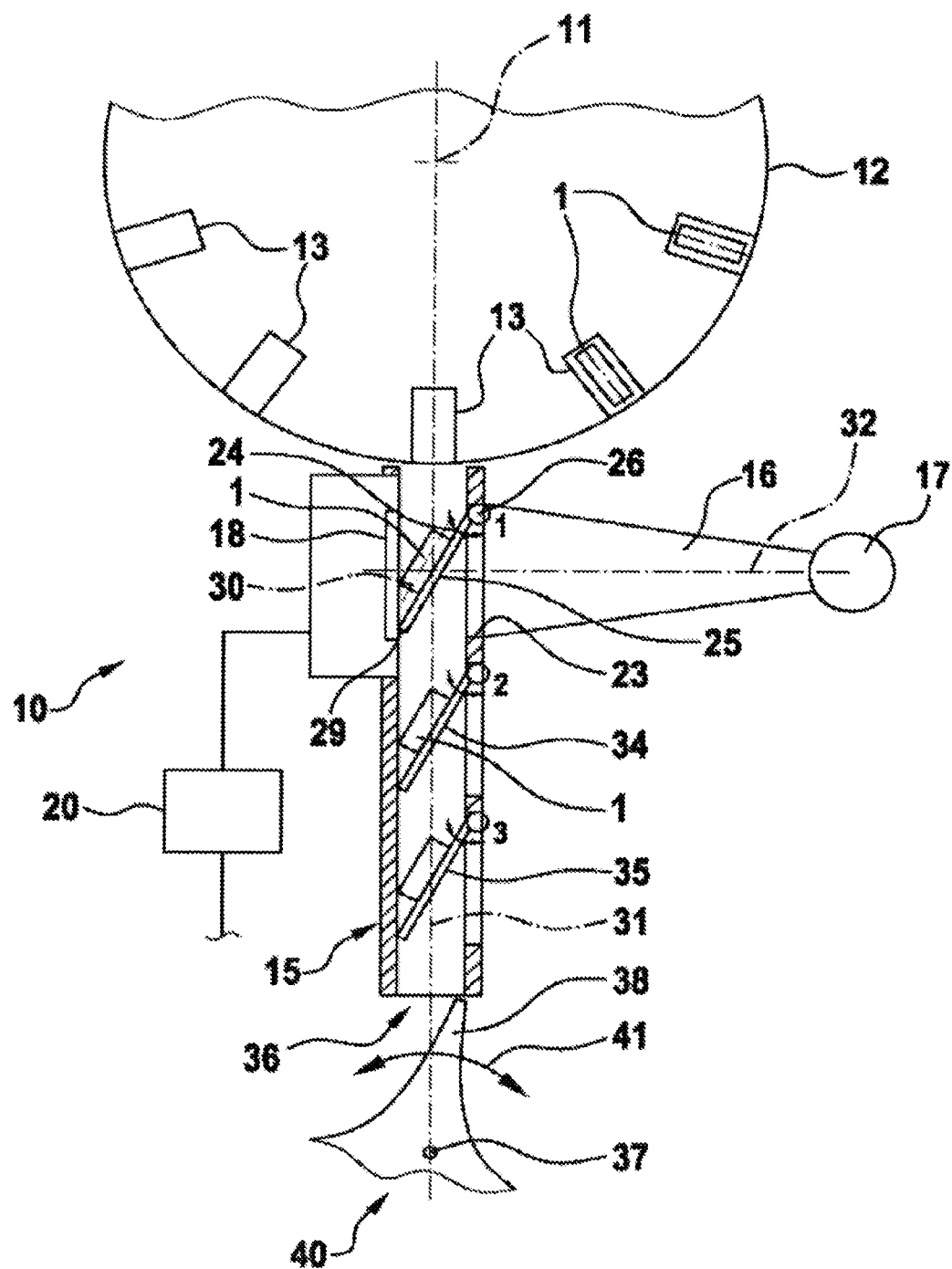

CONTROL DEVICE

BACKGROUND OF THE INVENTION

The invention relates to a control device comprising a radiation source which is embodied, in particular, as an X-ray source for irradiating a pharmaceutical product embodied, in particular, as a capsule, a detector for detecting radiation after irradiating the pharmaceutical product, a tube or shaft-shaped supply device which is preferably arranged vertically at least in the region of the beam path of the radiation source for feeding the pharmaceutical product into the beam path of the radiation source, and means for positioning and releasing the pharmaceutical product in the region of the radiation beam of the radiation source.

Such a control device is known from the German patent application DE 10 2009 045 809 A1 subsequently published by the applicant. The weight of capsules filled with a pharmaceutical can be determined by irradiating the capsules with X-rays using the known control device. In addition, it is possible to detect, for example, foreign particles or something similar which have entered into the capsules during filling. The control device known from the German patent application DE 10 2009 045 809 A1 comprises a tube or shaft-shaped transport element for transporting the capsules into the region of the X-ray source, said capsules being transported in the transport element in a vertically arranged row. That means that the transport element, with regard to the cross-section thereof, has to be adapted very precisely to the format of the pharmaceutical products to be examined. This adaptation is also then required in the previously known control device because the X-ray source irradiates the pharmaceutical product in a direction perpendicular to the longitudinal axis thereof.

The known control device exhibits a high level of performance for the format to be processed in each case. It is, however, required to adapt the transport device to the new format of the pharmaceutical products for each batch or format change. This generally occurs by replacing the transport device, which to this end is preferably embodied as a format part. The replacement of parts and the recalibration associated therewith during a format change require, however, a relatively high amount of effort and associated cost.

SUMMARY OF THE INVENTION

On the basis of the depicted prior art, the aim underlying the invention is therefore to further develop a control device such that said control device can be used for different formats of pharmaceutical products without a retrofitting or conversion of the supply device being required to meet this end. The control device meets this aim according to the invention by virtue of the fact that the tube or shaft-shaped supply device has a cross-section in the region of the beam path which is greater than the cross-section of the pharmaceutical product and by virtue of the fact that during irradiation, respectively only one pharmaceutical product is arranged in the region of the beam path of the radiation source. In other words, this means that the supply device has a cross-section designed in such a manner that said supply device can be used for all formats of the pharmaceutical products to be examined which have a smaller cross-section than said supply device.

With regard to positioning the pharmaceutical product in the region of the radiation beam, provision is made in a preferred structural design of the invention for the means for positioning and releasing the pharmaceutical product in the region of the beam path to comprise a stopping flap which can be pivoted or displaced perpendicularly to the direction of transportation of the products and the length of which is preferably greater than the length of the pharmaceutical product.

It is particularly advantageous if the stopping flap is permeable to the radiation of the radiation source. The stopping flap can thereby be arranged directly in the beam path of the radiation source, whereby on the one hand the constructional effort and expenditure are reduced and on the other hand the stopping flap can simultaneously serve as a supporting surface for the pharmaceutical object.

In a particularly advantageous structural design of the stopping flap, in which an integration of the stopping flap into the supply device is facilitated, provision is therefore made for said stopping flap to be arranged with the axis of rotation thereof in the region of the supply device, for said stopping flap, in the release position thereof, to form a part of the supply device and in the stopping position thereof to rest against an opposite wall of the supply device or against the detector with the side thereof facing away from the axis of rotation.

In order to obtain sufficient time for an evaluation of the measurement results after irradiating the pharmaceutical product and in so doing to particularly be able to discard the scanned pharmaceutical product if said product does not meet certain requirements, provision is further preferably made for additional stopping means for blocking the pharmaceutical product to be disposed downstream of the detector of the supply device in the direction of transportation of the products, said stopping means interacting with a good/bad removal device.

In order to facilitate a feeding of the individual pharmaceutical product into the beam path of the radiation source without requiring additional stopping means above the radiation source for this purpose, provision can furthermore be made for the pharmaceutical products to be fed into the region of the supply device by means of a transport device embodied as a progressively rotated transport wheel, said transport wheel having individual receptacles for the pharmaceutical objects.

In order to simplify the measuring process and the traceability of the results, it is furthermore particularly advantageous for a reference object to be arranged in the region of the detector for the purpose of comparison with the pharmaceutical product. Such a reference object preferably has similar radiation properties as the pharmaceutical product being measured and comprises, for example, regions of different thicknesses so that the result of the picture of the irradiated product can be compared to the reference object. As a result, conclusions can, e.g., be drawn concerning the weight of the pharmaceutical product.

BRIEF DESCRIPTION OF THE DRAWING

Further advantages, features and details of the invention ensue from the following description of preferred exemplary embodiments as well as on the basis of the drawing.

The FIGURE shows a simplified longitudinal section through an inventive capsule control device.

DETAILED DESCRIPTION

The capsule control device 10 is used to check pharmaceutical products 1. The pharmaceutical products 1 relate particularly to, however are not limited to, capsules that are filled with a pharmaceutical and if applicable additives in the form of hard gelatin capsules, tablets or the like, the net weight of which and/or other properties, e.g. the presence of foreign particles, are intended to be checked using the capsule control device 10.

The capsule control device 10 comprises a transport wheel 12 progressively rotatable in a horizontal axis of rotation, said transport wheel having a receptacle for each pharmaceutical product 1 on the outer periphery thereof. The transport wheel 12 is, for example, loaded with the pharmaceutical products 1 by means of a supply chute comprising a shaft-like region.

A supply device 15 designed as a tube or shaft-shaped transport device adjoins the transport wheel 12 perpendicularly below the axis of rotation 11 of said transport wheel 12. The supply device 15 serves to individually feed pharmaceutical products 1 into the region of the radiation beam 16 or rather the radiation beam cone of a radiation source, which is embodied, in particular, as an X-ray source 17. The pharmaceutical product 1 to be examined is irradiated by means of the X-rays produced by the X-ray source 17. In so doing, the X-rays which pass through the pharmaceutical product are detected by means of a detector 18, which is disposed on the side of the pharmaceutical product 1 opposite to the X-ray source 17.

The detector 18 is embodied, in particular, as an image recording detector 18 and is coupled to an electronic evaluation device 20, which serves to determine whether the pharmaceutical product 1 has the desired properties or not on the basis of the recorded or, respectively, detected image of the X-rays. To this end, provision can also be made for a reference object, which is not depicted in the FIGURE, to be arranged in the beam path 16 of the X-ray source 17, said reference object providing a comparison to the pharmaceutical product 1 to be respectively irradiated. The pharmaceutical product 1 and the reference object are thereby simultaneously, i.e. with a single image, irradiated or, respectively, captured using the detector 18.

The supply device 15 preferably has however, at least at the height of the X-ray source 17, a constant, in particular a rectangular, cross-section across the entire vertical length thereof. In this regard, the cross-section or the cross-sectional area of the supply device 15 is calculated in such a way that said cross-section is larger than the cross-sections of the pharmaceutical products 1 to be examined. In the exemplary embodiment depicted, the detector 18 forms a wall section of the supply device 15 on the side facing away from the X-ray source 17 by said supply device 15 comprising a corresponding recess or notch in the region of the detector 18.

On the side of the supply device 15 opposite to the detector 18, said supply device has a further recess 23 in which a pivotable stopping flap 25 is disposed in the direction of the double arrow 24. The stopping flap 25 which can be moved by means of a drive (not depicted) is thereby mounted in a horizontally disposed rotation of axis 26, which is arranged in the region of the recess 23 and has a length that is greater than the length of the pharmaceutical products 1 in order to form a flat supporting surface for the pharmaceutical product 1 when pivoting or to prevent said pharmaceutical product 1 from seizing in the supply device 15 in the stopping position of the stopping flap 25.

The stopping flap 25, which consists of a material permeable to the X-ray source 17, closes flush with the wall of the supply device 15 in the released position thereof.

In the stopping position of the stopping flap 25, which is depicted in the FIGURE, the lower edge 29 of the stopping flap 25, which faces away from the axis of rotation 26, contacts the detector 18 or the wall of the supply device 15 (the latter not depicted) or is arranged at a distance thereto which is small enough to prevent the pharmaceutical product 1 from falling through the gap formed as a result. The irradiation of the pharmaceutical product 1 by means of the X-ray source 17 takes place in the stopping position of the stopping flap 25. It can particularly be seen with the aid of the drawing that during the measuring process or rather during the irradiation, the longitudinal axis 30 of the pharmaceutical product 1 is disposed at an oblique angle with respect to the longitudinal axis 31 of the supply device 15, which is arranged in the vertical direction, as well as at an oblique angle with respect to the beam axis 32 of the X-ray source 17. The stopping flap 25 thereby forms a supporting surface for the pharmaceutical product 1. The aforementioned reference object is preferably disposed in an identical angular position with respect to the stopping flap 25 as the pharmaceutical product 1, if said stopping flap 25 is located in the stopping position thereof.

Two further stopping flaps 34, 35 are arranged below said stopping flap 25 in the direction of transportation of the products and are embodied substantially identical to the stopping flap 25 but do not have to consist of a material permeable to the X-ray source 17. The additional stopping flaps 34, 35 can also be actuated, in particular individually, via drives that are not depicted.

A flap 38 which is part of a removal device 40 is disposed at the outlet 36 of the supply device 15, said flap being disposed so as to pivot about an axis of rotation 37. The removal device 40 actuated, in particular, by the evaluation device 20 thereby pivots the flap 38 in accordance with the direction of the double arrow 41 in the one or other position depending on the result of the evaluation device 20; thus enabling pharmaceutical products 1 recognized as being "good" to pass through another additional transport path than the pharmaceutical products 1 recognized as being "bad".

The capsule control device 10 described up until now operates as follows: By means of the transport wheel 12, respectively one pharmaceutical product 1 is delivered from said transport wheel 12 into the supply device 15. In so doing, said pharmaceutical product falls into the region of the stopping flap 25 due to the force of its own weight. The stopping flap 25 is located initially in the stopping position thereof. After the pharmaceutical product 1 lies on the stopping flap, said product is exposed to radiation by means of the X-ray source 17, wherein the image captured by the detector 18 together with the image of the reference object is supplied to the evaluation device 20. The stopping flap 25 is subsequently pivoted into the release position thereof; thus enabling the pharmaceutical product 1 in a plurality of steps to be subsequently transported via the additional stopping flaps 34, 35 in the direction of the outlet 36 of the supply device 15.

After releasing the pharmaceutical product 1 by way of the stopping flap 25, the latter is immediately pivoted back into the stopping position thereof in order to be able to receive the next pharmaceutical product 1 to be examined. The two additional stopping flaps 34, 35 make it possible for the recorded image of the pharmaceutical product 1 to be evaluated or, respectively, examined by the evaluation device 20, the required period of time therefore being made possible by the two stopping flaps 34, 35. As soon as the result of the evaluation has been determined, the lower stopping flap 35 is pivoted into the release position thereof, wherein the flap 38 of the removal device 40 was already pivoted shortly in advance thereof into the corresponding "good" or "bad" position based on the result of the evaluation device 20.

The capsule control device 10 described up until now can be modified or adapted in a plurality of ways without deviating from the inventive concept. In particular, other supply devices besides the transport wheel 12 or other removal devices 40 are also conceivable. It is only essential that by means of the geometric construction of the supply device 15 having a cross-section which is greater than the cross-sectional area of the pharmaceutical product 1, pharmaceutical products 1 of different size can be transported with one and the same supply device 15 into the region of the radiation source and that the widest variety of formats of the pharmaceutical products 1 can be temporarily retained or rather the transport path thereof can be temporarily blocked by means of the stopping flap 25 which simultaneously forms a supporting surface for the pharmaceutical product 1 to be examined.

The invention claimed is:

1. A control device (10) comprising:
    a radiation source (17) for irradiating a pharmaceutical product (1),
    a detector (18) for detecting radiation after irradiating the pharmaceutical product (1),
    a tube or shaft-shaped supply device (15) for feeding said pharmaceutical product (1) into a beam path (16) of the radiation source (17), and
    a stopping flap (25) in the region of the radiation beam (16), the stopping flap (25) being pivotable or displaceable perpendicularly with respect to a direction of transportation of the pharmaceutical product (1) for positioning and releasing said pharmaceutical product (1) in the region of the beam path (16) of the radiation source (17) such that during irradiation, respectively only one pharmaceutical product (1) is arranged in the region of the beam path (16) of the radiation source (17),
    wherein the tube or shaft-shaped supply device (15) has a cross-section in the region of the beam path (16) which is greater than a cross-section of said pharmaceutical product (1) and
    wherein the stopping flap (25) is permeable to radiation of the radiation source (17).

2. The control device according to claim 1 characterized in that the stopping flap (25) forms a supporting surface for the pharmaceutical product (1) during irradiation.

3. The control device according to claim 2, characterized in that the stopping flap (25) is arranged with an axis of rotation (26) thereof in a region of the supply device (15), forms a part of the supply device (15) in a release position thereof and in a stopping position thereof rests against an opposite wall of said supply device (15) or against the detector (18) with a side thereof facing away from the axis of rotation (26).

4. The control device according to claim 1, characterized in that the supply device (15) has a rectangular cross-section at least in the region of the radiation beam (16) of the radiation source (17).

5. The control device according to claim 1, characterized in that the radiation source (17) exposes the pharmaceutical product (1) to radiation at an oblique angle in relation to a longitudinal axis (30) thereof.

6. The control device according to claim 1, characterized in that further stopping means (34, 35), which are provided for blocking the pharmaceutical product (1) and interact with a good/bad removal device (40), are disposed downstream of the detector (18) of the supply device (15) in a direction of transportation of said product.

7. The control device according to claim 1, characterized in that the pharmaceutical products (1) are fed into a region of the supply device (15) by means of a transport device embodied as a progressively rotated transport wheel (12), said transport wheel (12) having individual receptacles (13) for the pharmaceutical products (1).

8. The control device according to claim 1, characterized in that a reference object for comparison with the pharmaceutical product (1) is arranged in a region of the detector (18).

9. The control device according to claim 1 wherein the radiation source (17) is an X-ray source.

10. The control device according to claim 1 wherein the pharmaceutical product (1) is a capsule.

11. The control device according to claim 1 wherein the tube or shaft-shaped supply device (15) is arranged vertically at least in the region of the beam path (16) of the radiation source (17).

12. The control device according to claim 1, characterized in that a length of said stopping flap (25) is greater than a length of the pharmaceutical product (1).

* * * * *